US006982827B2

(12) United States Patent
Mora (10) Patent No.: US 6,982,827 B2
(45) Date of Patent: Jan. 3, 2006

(54) SURGICAL MICROSCOPE ARRANGEMENT AND INTERFACE UNIT FOR A SURGICAL MICROSCOPE (75) Inventor: Assad F. Mora, Santa Barbara, CA (US)

(73) Assignee: Carl-Zeiss-Stiftung, Heidenheim (DE)

( * ) Notice: Subject to any disclaimer, the term of this patent is extended or adjusted under 35 U.S.C. 154(b) by 52 days.

(21) Appl. No.: 10/294,709

(22) Filed: Nov. 15, 2002

(65) Prior Publication Data
US 2004/0095639 A1    May 20, 2004

(51) Int. Cl.
*G02B 21/00*    (2006.01)
(52) U.S. Cl. ...................................... 359/384; 354/368
(58) Field of Classification Search ................ 359/384, 359/368, 372, 374, 375
See application file for complete search history.

(56) References Cited

U.S. PATENT DOCUMENTS

| 4,167,302 | A  | * | 9/1979 | Karasawa ................... 359/377 |
| 4,170,336 | A  |   | 10/1979 | Malis |
| 4,170,337 | A  |   | 10/1979 | Davis |
| 4,576,450 | A  |   | 3/1986 | Westphal |
| 6,172,804 | B1 |   | 1/2001 | Schuck et al. |
| 6,421,173 | B1 | * | 7/2002 | Corbisiero et al. ......... 359/372 |
| 2003/0053203 | A1 | * | 3/2003 | Strobel et al. .............. 359/384 |

FOREIGN PATENT DOCUMENTS

| DE | 24 40 958 | 3/1976 |
| DE | 196 13 431 | 10/1996 |
| DE | 297 97 144 | 8/1998 |
| EP | 0 310 514 | 4/1989 |
| WO | WO 91 15150 | 10/1991 |

OTHER PUBLICATIONS

"Operation Microscope OPMI MD A new dimension in the field of operation microscopes", Medical technology, Zeiss, Germany.

* cited by examiner

*Primary Examiner*—Drew A. Dunn
*Assistant Examiner*—Joshua L. Pritchett
(74) *Attorney, Agent, or Firm*—Walter Ottesen (57) ABSTRACT A surgical microscope arrangement comprises a stand unit with a surgical microscope having an ocular unit and a tubular unit. The surgical microscope is carried by a stand unit in holding the ocular unit while allowing for pivoting of the tubular unit. When the tubular unit is pivoted, the ocular unit remains stationary. This can be achieved by providing an interface unit in the surgical microscope connecting the tubular unit with the ocular unit. The interface is formed as a rotary joint and includes a first portion which is to be connected to the ocular unit and the stand while the second portion of the interface unit is connected to the tubular unit of the microscope. The second portion of the interface unit can be pivoted with respect to the first portion of the interface unit.

21 Claims, 7 Drawing Sheets

SURGICAL MICROSCOPE ARRANGEMENT AND INTERFACE UNIT FOR A SURGICAL MICROSCOPE

FIELD OF THE INVENTION

This invention relates to a surgical microscope arrangement which includes a surgical microscope and a stand. The invention further relates to an interface unit for a surgical microscope. The interface unit connects an ocular viewing unit and a tubular unit of the surgical microscope while providing a viewing beam path.

BACKGROUND OF THE INVENTION

The surgical microscope arrangement OPMI® pico of Carl Zeiss includes a surgical microscope connected to a stand. This stand holds the surgical microscope at its tubular unit. The tubular unit and a pivotal ocular unit can be connected by means of an interface unit formed by a rotatable adapter and an angled optic. With such an angled optic, a view on object areas can be provided which are difficult to access. The rotatable adapter allows for rotation of the ocular unit with respect to the tubular unit around an axis parallel to a viewing beam path.

Surgical microscope arrangements connected to a stand have been also described in U.S. Pat. No. 4,035,057, U.S. Pat. No. 4,167,302, U.S. Pat. No. 4,170,336 and European patent publication 1 037 085.

U.S. Pat. No. 4,035,057 discloses a surgical microscope arrangement comprising an ocular viewing unit attached to a beam-splitter, which is connected to a magnification changer and a main objective lens unit. The surgical microscope arrangement is held by a stand having an arm connected to the magnification changer unit.

U.S. Pat. No. 4,167,302 relates to a surgical microscope arrangement in which the microscope body is mounted on a support member which is laterally and vertically swingable and slidable along its longitudinal axis. The microscope body includes an objective lens tube mounted on said support member and having a pair of objective lenses. For accommodating two different types of binocular tubes, the objective lens tube can be mounted on said support member at two different portions.

U.S. Pat. No. 4,170,336 discloses a surgical microscope arrangement which is connected to a stand by means of a C-shaped bracket holding the microscope in the lower part of the ocular unit. The C-shaped bracket includes a rod extending between arms on which the microscope is rotatably supported.

European patent publication 1 037 485 describes a surgical microscope arrangement comprising an ocular unit attached to a microscope body. The surgical microscope arrangement is connected to a stand by a set of rotatably arranged arms which hold the body of the microscope.

SUMMARY OF THE INVENTION

The improved surgical microscope, arrangement of this type according to the invention is characterized by the fact that the stand unit is carrying the surgical microscope and allows for pivoting the tubular unit with respect to the ocular unit and with respect to the stand unit while the ocular unit remains stationary. This can be achieved by providing an interface unit which is formed as a rotary joint and is connecting the tubular unit of the microscope with the ocular unit of the microscope. The interface unit has a first portion which is connected to the tubular unit and a second portion which is connected to the ocular unit. Preferably the rotary joint includes a holding element which is rigidly connected with the first portion of the interface unit. This holding element has an angular cross section engaging a ledge portion of the second portion of the interface unit. The holding element is holding the second portion of the interface unit against the first portion of the interface unit. This mechanism allows for rotating the first portion of said interface unit with respect to said second portion of said interface unit such that a pivot axis is formed.

The second portion includes means for mounting the surgical microscope arrangement on a stand. These means for mounting can include a threaded bore provided in the interface unit. Preferably, the pivot axis of the interface unit is arranged in parallel to an optical viewing beam path passing the interface unit. In an alternate embodiment, the pivot axis of the interface unit is arranged perpendicular to an optical viewing beam path passing the interface unit. In another preferred embodiment, the interface unit provides for a binocular viewing beam path. For deflecting the viewing beam path in the interface unit, an optical element arrangement is provided. Such optical element arrangement can include flat mirrors, prisms or a prism assembly. Preferably, the interface unit has a dove-tail coupling for connecting the first portion of the tubular unit to the interface.

BRIEF DESCRIPTION OF THE DRAWINGS

The invention will now be described with reference to the drawings wherein:

FIG. 6 is a side view.

FIGS. 12 and 13 illustrate the setup of an angled optic which is part of the surgical microscope arrangement shown in FIG. 9; and, FIG. 14 is an overall view of a third embodiment of a surgical microscope arrangement.

DESCRIPTION OF THE PREFERRED EMBODIMENTS OF THE INVENTION

Figure 1:
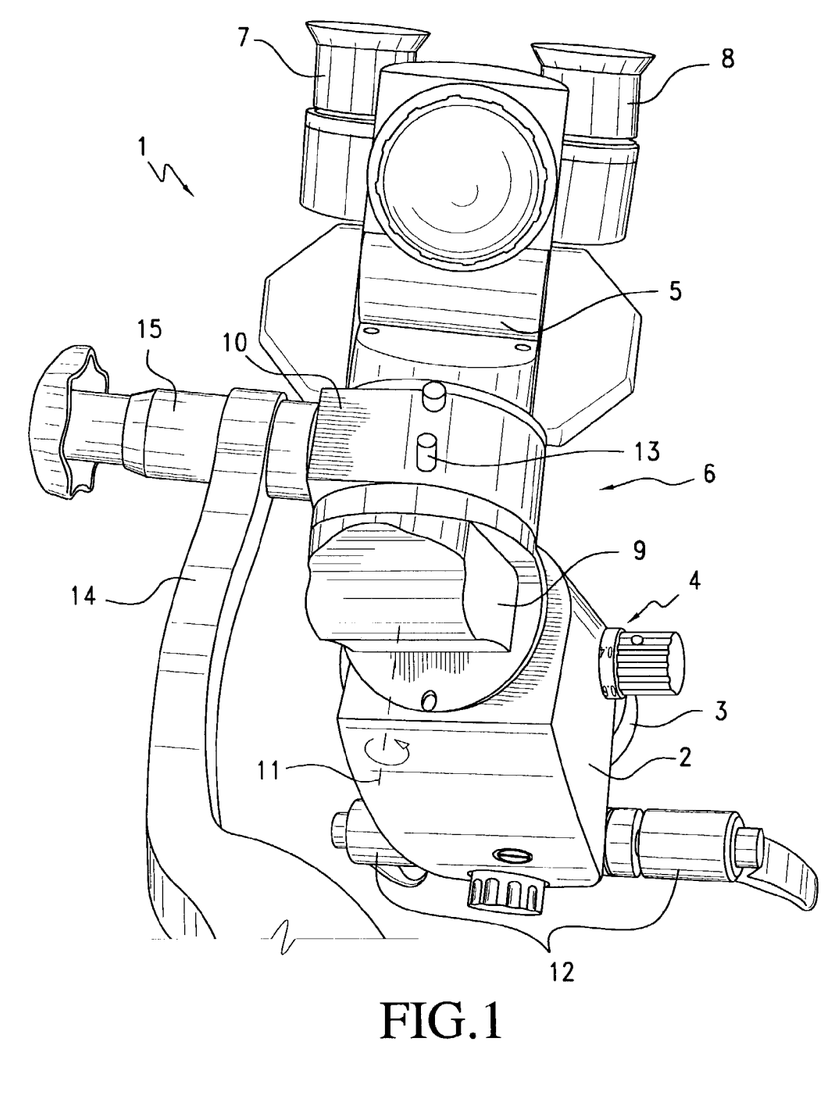
FIG. 1 is an overall view of a first embodiment of a surgical microscope arrangement comprising an interface unit for holding the surgical microscope on a stand.

FIG. 1 shows a first embodiment of a surgical microscope arrangement 1. The surgical microscope arrangement 1 includes a tubular unit 2 having a main objective lens system 3 and a magnification changer unit 4. The surgical microscope arrangement further includes, as an ocular unit, a pivotal binocular viewing unit 5 which is coupled to the tubular unit 2 by an interface unit 6. The binocular viewing unit has viewing ports 7 and 8. The interface unit 6 is formed as a rotary joint and includes a tubular portion 9 and an ocular portion 10. The rotary joint allows the tubular portion 9 of the interface unit 6 to pivot with respect to the ocular portion 10 about pivot axis 11. The tubular portion 9 of the interface unit 6 is connected to the tubular unit 2 with a first dovetail coupling. Correspondingly, the ocular portion 10 is connected to the ocular unit 5 with a second dovetail coupling. The tubular portion 9 carries the tubular unit 2. The tubular unit 2 includes handles 12 for comfortably pivoting the microscope and moving it while connected to an arm 14 of a stand. A clamping mechanism 13 is arranged on the ocular portion 10. This clamping mechanism provides for a friction force to fix the rotary joint connecting the tubular portion 9 and the ocular portion 10. The ocular portion 10 of the interface unit 6 is attached to the arm 14 of the stand by a fixing mechanism 15.

Figure 2:
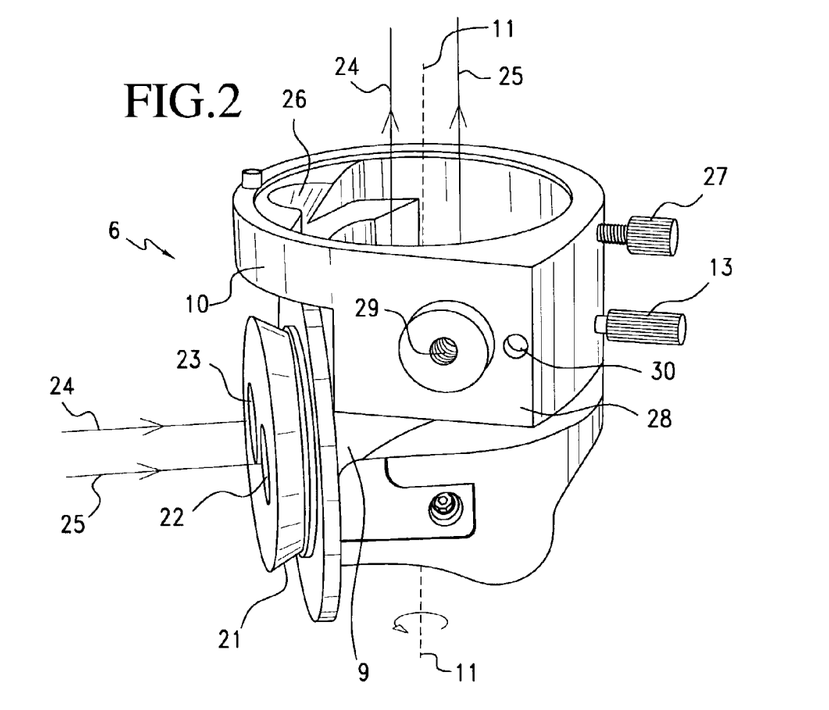
FIG. 2 shows a detailed perspective view of the interface unit of the surgical microscope arrangement in FIG. 1.

FIG. 2 is a detailed perspective view of the interface unit 6 shown in FIG. 1. Identical units which have been shown in FIG. 1 are depicted by the same reference numbers. The tubular portion 9 of the interface unit 6 has a male dove-tail coupling portion 21 for connecting the tubular unit 2 of the microscope. The dove-tail coupling portion 21 has two through bores 22, 23 for two parallel stereoscopic viewing beam paths 24, 25. Inside the tubular portion 9, an optical element arrangement in form of a pentaprism is provided for deflecting the beam paths towards the ocular portion 10. The interface unit 6 further includes a female dovetail coupling portion 26 with a coupling screw 27 on the ocular portion 10 for connecting a binocular viewing unit 5 of the microscope. On a side of the ocular portion 10, a mounting portion in form of a flat flange like section 28 with a threaded bore 29 and a detent 30 are provided. In order to fix the interface unit 6 to the stand, the fixing mechanism 15 is arranged on the arm 14 of the stand and includes a fixing screw which threadably engages the threaded bore 29 thereby pressing a flat portion of this arm against the flange like section and causing a detent to engage the detent bore 30. The pin and the screw form a two-point connection and ensure a firm and secure connection of the stand and the surgical microscope. The fixing mechanism 15 allows for easy removal and attachment of the surgical microscope. The rotary joint of the interface unit 6 has an axis of rotation 11 which is parallel to the optical beam paths (24, 25) in the ocular portion 10 of the interface unit 6.

Figure 3:
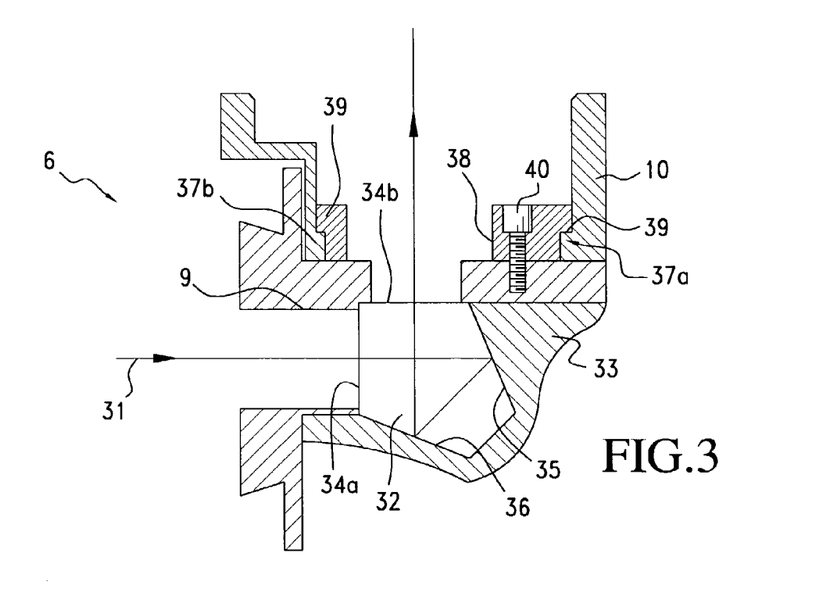
FIG. 3 is a side sectional view of the interface unit shown in FIG. 2.

FIG. 3 is a side sectional view of the interface unit 6 shown in FIG. 2. FIG. 3 shows a viewing beam path 31 through the optical element in form of a pentaprism 32 and explains the working principle of the rotary joint of the interface unit 6. Identical units, which are shown in FIG. 2, are depicted by the same reference numbers.

The viewing beam path 31 enters the tubular portion 9 and passes into the pentaprism 32 at first side 34*a* thereof. The pentaprism 32 is mounted in a cover 33. Light passing along a beam path 31 is twice reflected on the sides 35 and 36 before leaving the pentaprism 32 at its side 34*b* and then passes into the ocular portion 10 of the interface unit 6. The pentaprism 32 deflects the optical viewing beam path 31 in the tubular portion 9 by 90° into the ocular portion 10. Because the viewing beam path is reflected twice at the sides of the pentaprism 32, the optical image passed from the tubular portion 9 to the ocular portion 10 is side-correct.

In its part facing the tubular portion 9, the ocular portion 10 has a first internal stepped flange section 37*a* and a second internal stepped flange section 37*b*. A holding element 38 is provided at a bottom section of the ocular portion 10. This holding element 38 has a stepped cross section and is designed to trap and engage the circumferential flange section (37*a*, 37*b*) with a ledge 39. The holding element 38 is rigidly connected to the tubular portion 9 by a set of fixing screws 40. The holding element 38 holds the ocular portion 10 against the tubular portion 9 of the interface unit 6 with the set of screws 40. The holding element 38 allows for rotation of the tubular portion 9 relative to the ocular portion 10.

Figure 4:
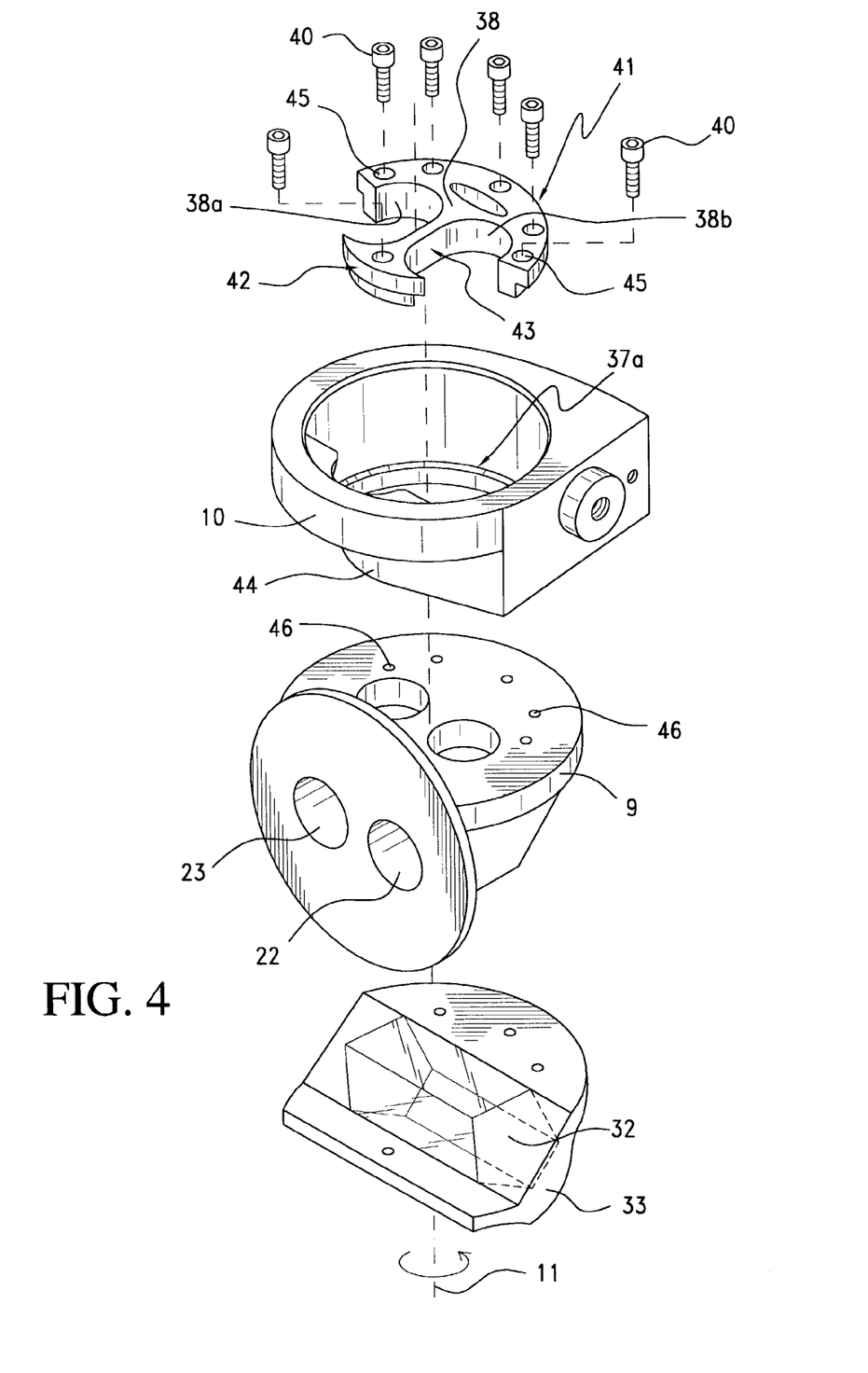
FIG. 4 shows an exploded view of the interface unit.

FIG. 4 is an exploded view of the interface unit 6. Again, identical units which are shown in the previous figures are identified by the same reference numbers. FIG. 4 shows the first bow-like shaped portion 41 and a second bow-like shaped portion 42 of the holding element 38. These portions of the holding element 38 are interconnected via a bridge like portion 43. The bow-like shaped portions 41 and 42 have different curvatures and form ledges. These ledges engage with flange sections (37*a*, 37*b*) at the bottom of the ocular portion 10 as shown in FIG. 3. The curvature of these flange sections corresponds to the curvature of the bow-like shaped portions.

The overall form of the holding element 38 is adapted to the form of the inner space in the lower bottom section of the ocular portion 10. The cross section of this space is non-circular because the ocular portion has a bay 44 to provide space for the dovetail coupling section of the tubular portion 9 thus allowing for rotational movement of the tubular portion 9 with respect to the ocular portion 10. The holding element 38 holds and engages the tubular portion 9 against the ocular portion 10.

The holding element 38 has bores 45 for a set of the fixing screws 40 which threadably engage threaded bores 46 provided in the tubular portion 9. On the holding element 38, curved openings (38*a*, 38*b*) are provided to allow for an unobstructed passage of viewing beam paths (24, 25) shown in FIG. 2.

The tubular portion 9, the ocular portion 10 and the cover 33 with the pentaprism 32 form a light-tight enclosure of the optical viewing beam path. This prevents the penetration of ambient light to the viewing beam path through the interface unit 6. Preferably, the cover 33, the tubular portion 9 and the ocular portion 10 are made of aluminum while the holding element 38 is made of stainless steel. This ensures an easy movement of the rotational joint and avoids jamming.

A pivoting of the tubular portion 9 with respect to the ocular portion 10 causes a rotation of the microscope image in the inter image plane of the surgical microscope.

Figure 5:
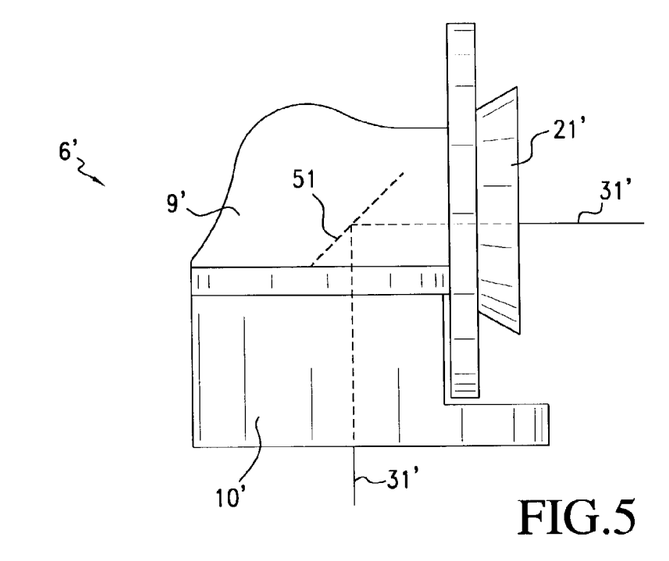
FIG. 5 is a side elevation view of an alternative embodiment of the interface unit.

FIG. 5 is a side elevation view of an alternate interface unit embodiment 6'. The portions of the interface unit 6' which correspond to portions of the interface unit described with respect to FIGS. 2 to 4 are identified by corresponding but primed reference numerals. The interface unit 6' includes a tubular unit 9' and an ocular unit 10' which are rotatably connected.

Instead of a pentaprism, a flat mirror 51 is mounted in the tubular portion 9' of the interface unit 6'. This flat mirror 51 deflects an optical viewing beam path 31' by 90°. However, since the viewing beam path is reflected an uneven number of times, there is no side-correct transfer of an optical image.

It may be understood, that in general, instead of a flat mirror, a prism or any other suitable arrangement of optical elements may be used for guiding the optical viewing beam path from the tubular portion to the ocular portion of the interface unit.

Figure 6:
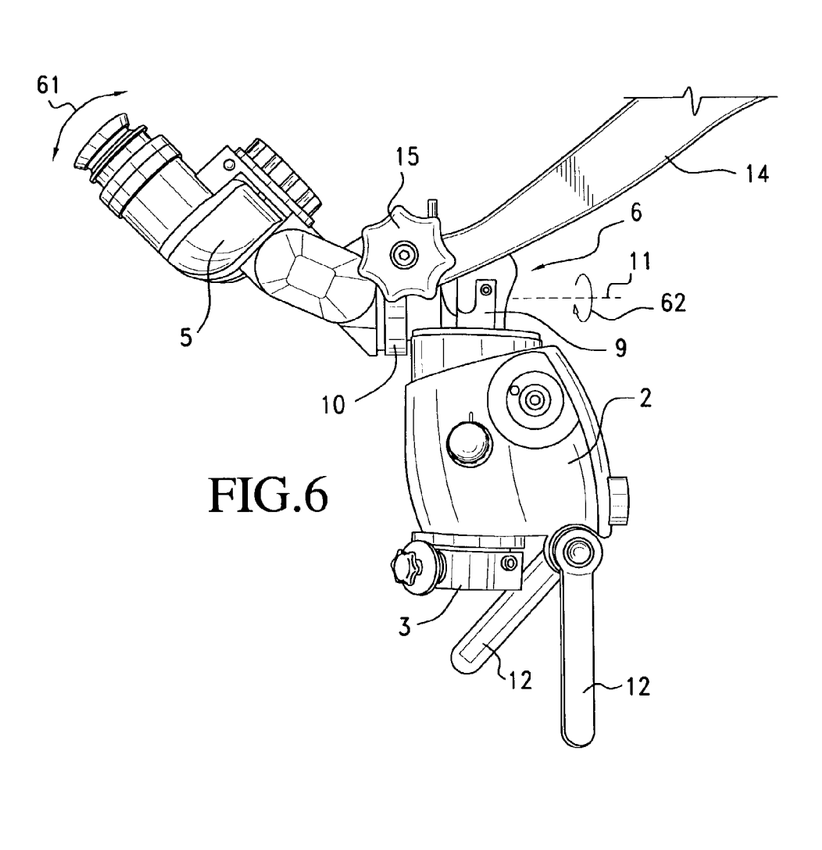
Figure 7:
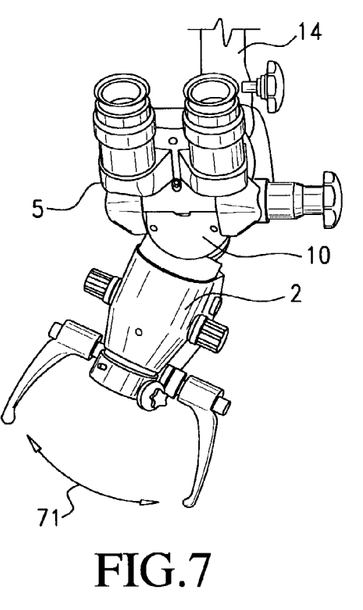
FIG. 7 is a front view and FIG. 8 is a back view of the surgical microscope arrangement with the interface unit illustrating how the tubular unit of the surgical microscope arrangement may be pivoted with respect to the ocular unit.
Figure 8:
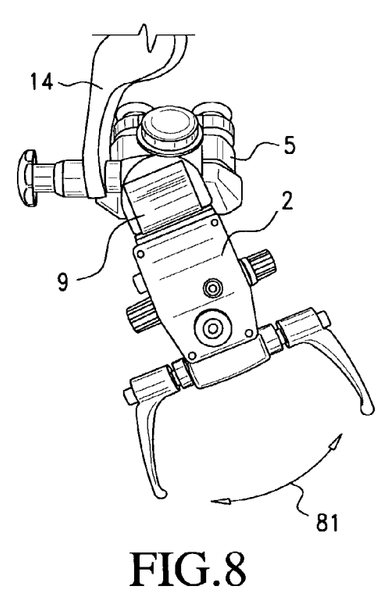

FIGS. 6, 7 and 8 show a surgical microscope arrangement which includes an above described interface unit. Identical elements, which have been described previously are identified by the same reference numbers. FIGS. 6 to 8 illustrate the motional degree of freedom for the tubular unit 2 of the microscope with respect to its ocular unit 5 while the microscope is attached to the arm of the stand.

FIG. 6 is a side view of the surgical microscope arrangement which is held by the fixing mechanism 15 on the arm 14 of the stand. The fixing mechanism 15 includes an ergonomically-shaped head. It incorporates a tension adjustment mechanism that increases or decreases the amount of friction between the arm 14 and the fixing screw. In this way, the fixing mechanism allows smooth pivoting balance when the microscope is rotated about an axis parallel to this fixing screw.

In order to provide a comfortable viewing angle, the pivotal binocular viewing unit 5 can be pivoted as indicated by arrow 61. Furthermore, the tubular unit 2 can be pivoted about the pivot axis 11 also shown in FIGS. 1 and 2 and indicated by arrow 62 while the ocular unit 5 of the surgical microscope remains stationary. This is achieved in that the surgical microscope is not connected to the stand through the tubular unit but through the interface unit 6. This allows for changing the direction of view of the surgical microscope while the corresponding ocular unit remains fixed.

As shown in FIGS. 7 and 8, a physician working with the microscope can pivotally adjust the ocular unit 5 for an ergonomic working position and is free to change the viewing direction by pivoting the tubular unit 2 of the instrument about pivot axis 11 as indicated by arrows 71 and 81. The physician can do this without shifting the head or otherwise changing the working position of the physician's body since the position of the ocular unit 5 remains fixed. Such movability of the tubular unit 2 is especially of interest in dental procedures.

Figure 9:
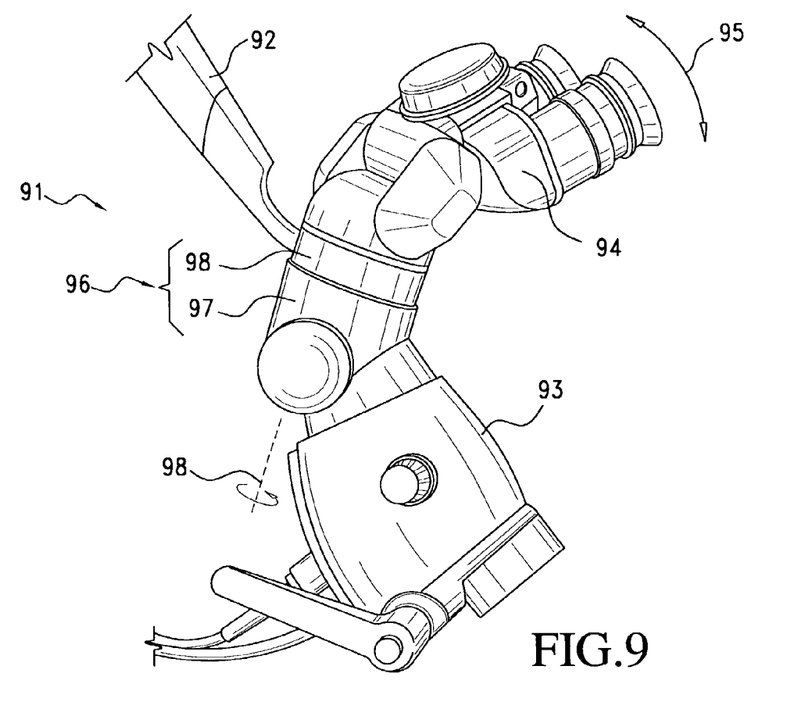
FIG. 9 is an overall view of a second embodiment of a surgical microscope arrangement.

FIG. 9 shows a second embodiment of a surgical microscope 91 attached to the arm 92 of a stand. The surgical microscope 91 includes a tubular unit 93 and an ocular unit 94 which can be pivoted according to arrow 95. The tubular unit 93 and the ocular unit 94 are connected by an interface unit 96 which comprises angled optic 97 and a rotatable adapter 98. The rotatable adapter 98 includes means for connecting the surgical microscope 91 to a stand. The rotatable adapter 98 allows for rotation of the angled optic 97 with the tubular unit 93 attached thereto about the adapter 98 while the ocular unit 94 remains stationary. The angled optic 97 deflects a binocular viewing beam path by an angle of about 120° through the interface unit 96.

Figure 10:
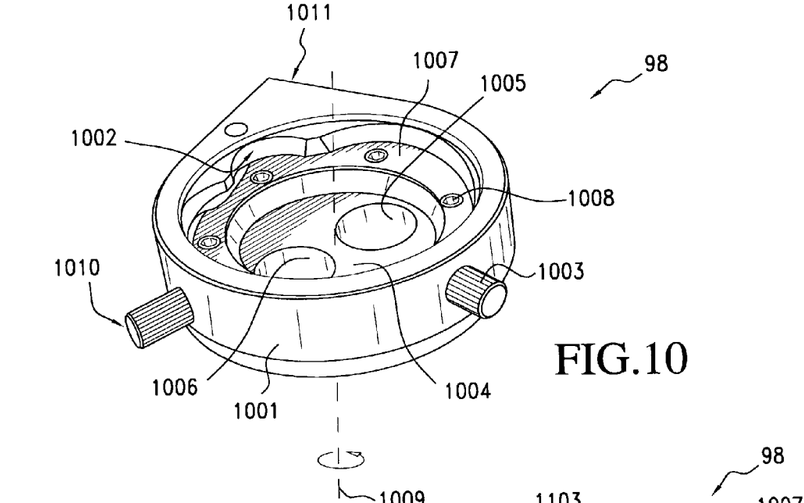
FIG. 10 is a detailed perspective view of a rotation coupling in the surgical microscope arrangement shown in FIG. 9.

FIG. 10 is a perspective view of the rotatable adapter 98 of the interface unit 96 in FIG. 9. The rotatable adapter 98 is formed by a first ocular portion 1001 which features a female dove-tail coupling portion 1002 for connecting the ocular unit 94 of the microscope shown in FIG. 9. This dovetail coupling portion 1002 includes a fixing screw 1003. The rotatable adapter 98 further includes a second portion 1004 which has a male dove-tail coupling portion for connecting the angled optic 97. In FIG. 10, a section of this second portion 1004 which faces toward the interior of the rotatable adapter 98 can be seen. In this second portion 1004, there are two through bores 1005 and 1006 for a binocular viewing beam path.

The second portion 1004 of the rotatable adapter is coupled to the first portion 1001 by a ring shaped holding element 1007. This ring shaped holding element 1007 engages a circumferential flange section 1101 (see FIG. 11) in the interior of the first ocular portion 1001 of the rotatable adapter. The holding element 1007 is rigidly connected to the portion 1004 of the rotatable adapter via fixing screws 1008 and holds the second portion 1004 against the ocular portion 1001 of the rotatable adapter. In this way, a rotary joint is formed. The second portion 1004 can be rotated with respect to the first portion 1001 about the rotational axis 1009.

The rotatable adapter 98 further includes a fixing mechanism 1010 which engages the ring shaped holding element 1007 for locking the rotary joint.

On a section 1011 of the first ocular portion 1001, a mounting portion is provided for connecting the rotatable adapter to the arm of the stand for a surgical microscope. This mounting portion corresponds to the one of the interface unit shown in FIG. 2.

Figure 11:
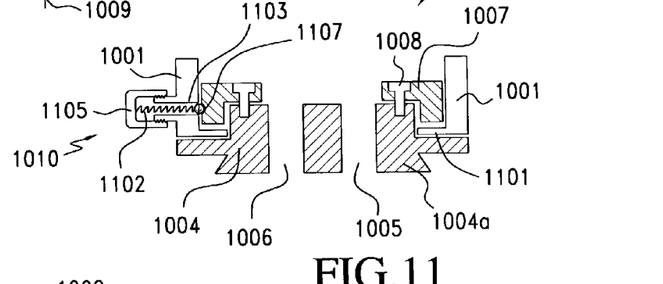
FIG. 11 is a sectional view of the rotation coupling presented in FIG. 10.

FIG. 11 is a sectional view of the rotatable adapter presented in FIG. 10. Identical elements, which have been shown in FIG. 10, are depicted by the same reference numbers.

The first tubular portion 1001 of the rotatable adapter has a circumferential flange section 1101. This circumferential flange section 1101 is engaged by the ring shaped holding element 1007 which is rigidly connected to the second portion 1004 of the rotatable adapter by means of fixing screws 1008. The second portion 1004 includes a male dove-tail coupling portion 1004a.

The fixing mechanism 1010 includes a spring 1102 which presses a detent pin 1103 into one of several recesses 1107 provided on the holding element 1007. The tension of the spring 1102 can be adjusted with a hollow nut 1105 engaging the spring 1102.

Figure 12:
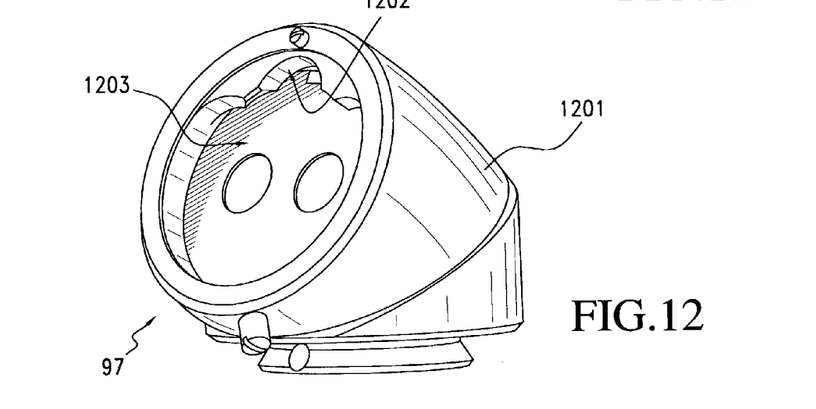

FIG. 12 shows the angled optics in the surgical microscope arrangement presented in FIG. 9. The angled optic 97 includes a hollow body 1201 having a female dove-tail coupling portion 1202. This hollow body 1201 accommodates an inner structure 1203 which is shown in detail in FIG. 13.

Figures 13, 14:
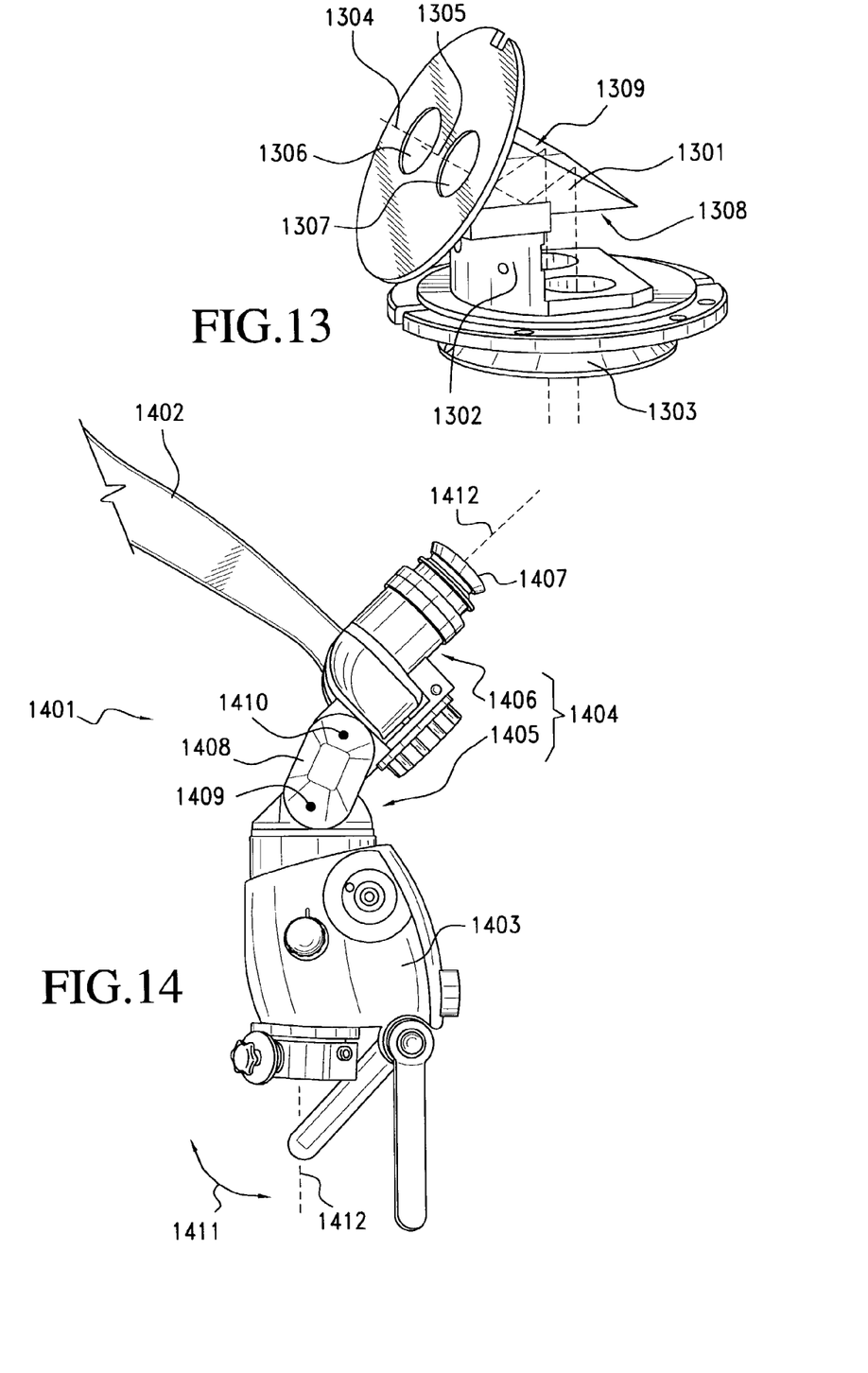

This inner structure 1203 includes a deflection prism 1301 which is mounted on a base portion 1302 forming a male dove-tail coupling portion 1303. The deflection prisms deflect viewing beam paths 1304, 1305 entering the angled optics through openings 1306 and 1307, respectively, towards the base portion 1302, whereby a viewing beam path is reflected twice on the sides 1308 and 1309 of the prism 1301 so that there is side correct transmission of an optical image.

FIG. 14 shows a third embodiment of a surgical microscope 1401 attached to the arm 1402 of a stand. The surgical microscope 1401 includes a tubular unit 1403 which is connected to an ocular element unit 1404. The ocular element unit 1404 includes an interface unit 1405 forming an ocular base unit and an ocular unit 1406. The ocular unit 1406 comprises a first viewing port 1407 and a second viewing port which is not shown. The interface unit 1405 and the ocular unit 1406 are connected via a first holding element 1408 and a second holding element which is not shown in FIG. 14. These holding elements include optics to guide a viewing beam path passing from the interface unit 1405 to the viewing port unit 1406. With pivot joints 1409 and 1410, the holding elements (1408) are articulated both at the interface unit 1405 and the ocular unit 1406. At the ocular unit 1406, the surgical microscope 1401 is connected to the arm 1402 of the stand. As indicated by arrow 1411, this allows the tubular unit 1403 of the surgical microscope 1401 to pivot relative to the ocular unit 1404 and the stand about an axis which is perpendicular to the viewing beam path 1412 of the surgical microscope. While pivoting the tubular unit 1403 as indicated by arrow 1411, the viewing ports (1407) remain stationary.

It is understood that the foregoing description is that of the preferred embodiments of the invention and that various changes and modifications may be made thereto without departing from the spirit and scope of the invention as defined in the appended claims.

What is claimed is:

1. A surgical microscope arrangement comprising:
   a stand having an arm;
   a surgical microscope including a viewing assembly and a tubular unit;
   said arm supporting said surgical microscope at a fixed position in space;
   said surgical microscope further including an interface unit comprising an ocular portion connected to said viewing assembly and a tubular portion connected to said tubular unit;
   said ocular portion and said tubular portion conjointly defining a rotary joint; and,
   said arm including a releasable attaching device for rigidly attaching said surgical microscope to said arm directly at said ocular portion so as to permit said tubular portion and said tubular unit to be rotated at said rotary joint while said ocular portion and said viewing assembly remain stationary in space with said arm.

2. The surgical microscope arrangement of claim 1, said interface unit connecting said tubular unit to said viewing assembly; and,
   said interface unit including optics defining a viewing beam path connecting said tubular unit to said viewing assembly.

3. The surgical microscope arrangement of claim 2, said viewing beam path being a binocular viewing beam path between said tubular unit and said viewing assembly.

4. The surgical microscope arrangement of claim 2, wherein said optics comprises an optical unit for deflecting said viewing beam path through said interface unit between said viewing assembly and said tubular unit.

5. The surgical microscope arrangement of claim 4, wherein said optical unit includes a mirror deflecting said viewing beam path.

6. The surgical microscope arrangement of claim 4, wherein said optical unit includes a prism deflecting said viewing beam path.

7. The surgical microscope arrangement of claim 2, wherein said rotary joint defines a rotational axis parallel to said viewing beam path.

8. The surgical microscope arrangement of claim 2, wherein said rotary joint includes a holding element which is rigidly connected to said tubular portion of said interface unit; and,
   said holding element having an angular cross section engaging a ledge portion of said ocular portion of said interface unit for holding said ocular portion of said interface unit against said tubular portion of said interface unit and allowing for rotating said tubular portion of said interface unit with respect to said ocular portion of said interface unit and said stand.

9. The surgical microscope of claim 2, wherein said interface unit has an elbow shape; and, said optics comprises an optical unit for deflecting said viewing beam path through the elbow-shaped interface unit.

10. The surgical microscope arrangement of claim 1, wherein a first dove-tail coupling portion is provided for connecting said tubular portion of said interface unit to said tubular unit and a second dovetail coupling portion is provided for connecting said ocular portion of said interface unit to said viewing assembly.

11. The surgical microscope of claim 1, wherein said releasable attaching device includes a threaded bore for receiving a screw.

12. An interface unit for connecting a tubular unit of a surgical microscope to a viewing assembly of the surgical microscope, the interface unit comprising:
   a mounting portion including mounting elements for mounting said interface unit to a stand so as to place said surgical microscope at a fixed position in space;
   an ocular portion for connecting said interface unit to said viewing assembly and a tubular portion for connecting said interface unit to said tubular unit;
   said ocular portion and said tubular portion conjointly defining a rotary joint;
   said interface unit including optics defining a viewing beam path connecting said tubular unit to said viewing assembly; and,
   said mounting elements being disposed on said ocular portion so as to permit rigidly attaching said interface unit to said stand directly at said ocular portion so as to permit said tubular portion and said tubular unit to be rotated at said rotary joint while said ocular portion and said viewing assembly remain stationary in space with said stand.

13. The interface unit of claim 12, further comprising providing a binocular viewing beam path between said tubular unit of said surgical microscope and said viewing assembly of said surgical microscope.

14. The interface unit of claim 13, wherein said rotary joint includes a holding element which is rigidly connected with said tubular portion of said interface unit; and, said holding element has an angular cross section engaging a ledge portion of said ocular portion of said interface unit for holding said ocular portion of said interface unit against said tubular portion of said interface unit and allowing for rotating said tubular portion of said interface unit with respect to said ocular portion of said interface unit.

15. The interface unit of claim 13, wherein said rotary joint defines a rotational axis which is arranged in parallel to a portion of said viewing beam path.

16. The interface unit of claim 13, wherein said tubular portion of said interface unit comprises an optical element arrangement for deflecting an optical beam path from said tubular portion of said interface unit to said ocular portion of said interface unit.

17. The interface unit of claim 16, wherein said optical element arrangement includes a mirror deflecting said optical beam path.

18. The interface unit of claim 17, wherein said optical element arrangement includes a prism deflecting said optical beam path.

19. The interface unit of claim 13, wherein a dove-tail coupling is provided for connecting said tubular portion of said interface unit with said tubular unit.

20. The interface unit of claim 12, wherein said mounting elements include a threaded bore in said ocular portion for receiving a fixation screw.

21. A surgical microscope arrangement comprising:
a surgical microscope including a viewing assembly and a tubular unit;
a stand having an arm supporting said surgical microscope thereon at a fixed position in space;
said viewing assembly and said tubular unit conjointly defining an interface;
an interface unit mounted at said interface and defining a rotary joint for allowing said tubular unit to pivot relative to said viewing assembly and said stand while said viewing assembly remains stationary;
said interface unit connecting said tubular unit to said viewing assembly;
said interface unit including optics defining a viewing beam path connecting said tubular unit to said viewing assembly; and,
fastening means for connecting said interface unit to said arm of said stand so as to permit said tubular unit to be rotated at said rotary joint while said viewing assembly remains stationary in space with said arm.

* * * * *

UNITED STATES PATENT AND TRADEMARK OFFICE
CERTIFICATE OF CORRECTION

PATENT NO. : 6,982,827 B2
DATED : January 3, 2006
INVENTOR(S) : Assad F. Mora

It is certified that error appears in the above-identified patent and that said Letters Patent is hereby corrected as shown below:

Title page,
Item [56], References Cited, FOREIGN PATENT DOCUMENTS, add -- EP 1 037 085 09/2000 --.

Column 1,
Line 59, delete "microscope," and insert -- microscope --.

Signed and Sealed this

Fourteenth Day of March, 2006

JON W. DUDAS
*Director of the United States Patent and Trademark Office*